United States Patent [19]

Goto et al.

[11] Patent Number: 5,213,708
[45] Date of Patent: May 25, 1993

[54] LIQUID CRYSTALLINE COMPOUND HAVING NEGATIVE DIELECTRIC ANISOTROPY VALUE

[75] Inventors: Yasuyuki Goto; Makoto Ushioda, both of Chiba, Japan

[73] Assignee: Chisso Corporation, Ohsaka, Japan

[21] Appl. No.: 794,622

[22] Filed: Nov. 18, 1991

Related U.S. Application Data

[63] Continuation of Ser. No. 475,944, Feb. 6, 1990, abandoned.

[30] Foreign Application Priority Data

Feb. 9, 1989 [JP] Japan .................................. 1-30675

[51] Int. Cl.$^5$ .................... C09K 19/34; C07D 237/008
[52] U.S. Cl. ................................. 252/299.61; 544/224
[58] Field of Search ...................... 252/299.61, 299.63; 544/224, 239

[56] References Cited

U.S. PATENT DOCUMENTS

| | | | |
|---|---|---|---|
| 4,818,429 | 4/1989 | Saito et al. | 252/299.61 |
| 4,834,904 | 5/1989 | Krause et al. | 252/299.01 |
| 4,943,384 | 7/1990 | Sucrow et al. | 252/299.61 |
| 5,055,221 | 10/1991 | Scheuble et al. | 252/299.61 |

Primary Examiner—Robert L. Stoll
Assistant Examiner—C. Harris
Attorney, Agent, or Firm—Wenderoth, Lind & Ponack

[57] ABSTRACT

The present invention provides a liquid crystalline compound having a large negative dielectric anisotropy value, a low viscosity and a large birefringence value and a liquid crystal composition suitable as an element constituting light switching elements. The liquid crystalline compound is expressed by the formula

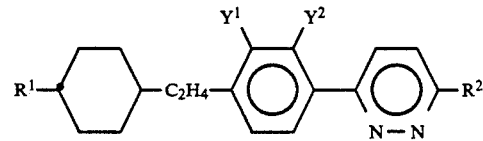

wherein $R^1$ and $R^2$ each independently represent an alkyl group or an alkoxy group each of 1 to 15 carbon atoms and $Y_1$ and $Y^2$ each independently represent H or F.

4 Claims, No Drawings

LIQUID CRYSTALLINE COMPOUND HAVING NEGATIVE DIELECTRIC ANISOTROPY VALUE

This application is a continuation of now abandoned application Ser. No. 07/475,944 filed Feb. 6, 1990.

BACKGROUND OF THE INVENTION

1. Field of the Invention

This invention relates to a novel liquid crystalline compound having a negative dielectric anisotropy value and a liquid crystal composition containing the same. The liquid crystalline compound referred to herein includes compounds exhibiting a liquid crystal phase by themselves and compounds which exhibit no liquid crystal phase by themselves, but are similar in structure to compounds exhibiting a liquid crystal phase. More particularly, it relates to a liquid crystal material usable for a liquid crystal display element utilizing an electrically controlled birefringence effect.

2. Description of the Related Art

An electrically controlled birefringence mode (hereinafter abbreviated to ECB mode) using a negative dielectric anisotropy value (dielectric anisotropy value being hereinafter abbreviated to $\Delta\epsilon$) was announced in 1971 (M. Schiekel & K. Fahrenschon, Appl. Phys. Lett., 19 (1971) 391), but since in this mode, a stabilized perpendicular alignment was hardly obtained and the liquid crystal viscosity was high, etc., it could not cope with a twisted nematic mode (hereinafter abbreviated to TN mode).

In recent years, however, due to advances in of perpendicular alignment technique, trial devices for a large capacity display element of ECB mode have been announced (Hp. Schad, M. Kauffmann & P. Eglin, Proc. 13, Freiburger Arbeitstagung Flussigkristalle, Freiburg (1982) 26, J. F. Clerc & J. C. Deutch, Proc. Eurodisplay, 87, London (1987) 111, Kinoshita, Matsumoto et al, Preprints for the 14th Liquid Crystal Symposium (1988) 72, Nikkei Microdevice, January, 1988, p. 69). According to these reports, the following matters are mentioned as the specific features of ECB mode:

(1) The voltage-light transmittance dependency is so steep as that of Supertwisted nematic mode (hereinafter abbreviated to STN mode) that drive at a high duty ratio is possible.

(2) There is no hysterisis as observed in STN mode having a large twist angle.

(3) Since the liquid crystal molecules are perpendicularly aligned, the light transmittance at the time of OFF is ideally low as compared with those of TN mode and STN mode, to obtain a high contrast ratio.

(4) Color display is possible.

(5) Viewing angle is broad.

As described above, ECB mode has characteristics suitable for realizing a panel having a large capacity and a large area.

Further, characteristics required for liquid crystal compositions for ECB mode are as follows:

(1) The viscosity is as low as possible in the aspect of response rate.

(2) The $\Delta\epsilon$ is advantageously negative and large in the aspect of the threshold voltage, and the lower the ratio of the $\Delta\epsilon$ to the dielectric constant in the direction of the major axis of molecules ($\epsilon_{//}$), the better the steepness of the voltage-light transmittance characteristic.

(3) Since a larger optical anisotropy value (hereinafter abbreviated to $\Delta n$) makes it possible to decrease cell thickness, such a large $\Delta n$ value is advantageous in the aspect of the response rate, because the response rate is inversely proportional to the square of the cell thickness. Further, the larger $\Delta n$ value is preferred also in the aspect of the steepness of the voltage-light transmittance dependency.

)4) As for the elastic constant, the higher the ratio of the elastic constants of the bend and spray ($K_{33}/K_{11}$), the better the steepness of the voltage-light transmittance dependency.

At present, however, there is no compound which satisfies all of the characteristics required for these items, and actually, liquid crystal compositions obtained by mixing several kinds of liquid crystal compounds or mixing several kinds of liquid crystal compounds with compounds similar to liquid crystals have been used.

As for liquid crystalline compounds thus far prepared having a negative $\Delta\epsilon$ to some extent, compounds having a 2,3-dicyanophenyl group in the molecular structure thereof, cyclohexane derivatives having a cyano group at the axial position thereof, pyridazine derivatives, etc. have been known. However, while compounds having a 2,3-dicyanophenyl group in the molecular structure thereof (Japanese patent application laid-open No. Sho 59-10557/1984) have a large negative $\Delta\epsilon$, they have a disadvantage of having an inferior solubility and a high viscosity. Further, cyclohexane derivatives having a cyano group at the axial position thereof (R. Eidenschink, G. Haas, M. Romer, B. Scheuble, Angew. Chem. 96 (1984) 151) have a negative $\Delta\epsilon$ which is not so large, in spite of having a molecular structure having a cyano group in the perpendicular direction of the molecule. Further, pyridazine derivatives (Japanese patent application laid-open No. Sho 59-106469/1984) have drawbacks that they mostly have no liquid crystal phase and when mixed with other liquid crystalline compounds, reduce the clearing point of the liquid crystal phase thereof. Further, a compound having a pyridazine ring

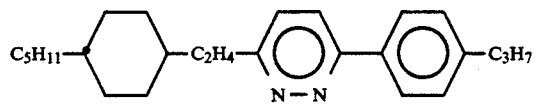

is disclosed in Z. Chem., 26, Jg (1986) 21 and is said to exhibit smectic phase, but its characteristics are unclarified.

SUMMARY OF THE INVENTION

The object of the present invention is to provide a liquid crystalline compound having a large negative $\Delta\epsilon$, a low viscosity, a large $\Delta\epsilon$ and a superior compatibility when mixed with one another and with other liquid crystalline compounds.

The present invention resides in:

a liquid crystalline compound having a negative dielectric anisotropy value, expressed by the formula

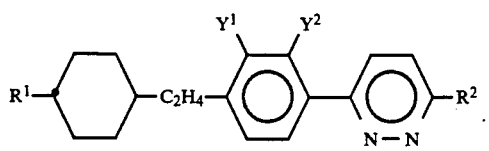

(I)

wherein $R^1$ and $R^2$ each independently represent an alkyl group or an alkoxy group each of 1 to 15 carbon atoms and $Y_1$ and $Y^2$ each independently represent H or F, and a liquid crystalline composition containing at least one of the above compounds.

DETAILED DESCRIPTION OF THE PREFERRED EMBODIMENTS

The compound of the present invention has not only a specific feature of having a negative $\Delta\epsilon$ as large as −7 when extrapolated, but also has specific features of having a relatively low viscosity of 42.1 cP for a three-ring compound and a $\Delta n$ as large as 0.205, for example; thus, the compound has well-balanced specific features desired for a component of liquid crystal materials for display elements according to ECB mode.

Among the compounds of the formula (I), those having one or two Fs in the 1,4-diphenylene group of the molecule, i.e. those of the formula (I) wherein at least one of $Y_1$ and $Y^2$ is F, have a superior compatibility not only with one another but also with other already known liquid crystalline compounds and, further have a low viscosity.

$R^1$ and $R^2$ in the formula (I) is preferably a linear alkyl group or alkoxy group each of 1 to 8 carbon atoms and $R^1$ is more preferably a linear alkyl group of 2 to 5 carbon atoms. Further, since compounds of the formula (I) having branched $R^1$ and $R^2$ have an improved solubility in liquid crystal materials, they are useful in some cases, and particularly when such $R^1$ and $R^2$ are optically active groups, the compounds having such $R^1$ and $R^2$ are useful as a chiral dopant.

The liquid crystal composition of the present invention contains the compound of the formula (I) in a proportion of 0.1 to 99%, preferably 1 to 40%, more preferably 5 to 30% each by weight.

As for compounds used in admixture with the compound of the formula (I) as components of the liquid crystal composition, known compounds expressed by the following formulas (i)-(xii) are listed:

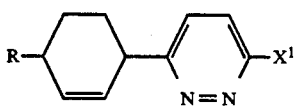
(i)

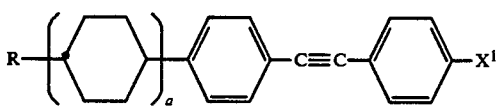
(ii)

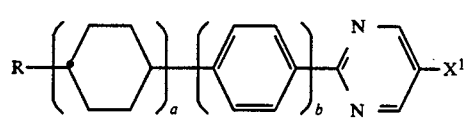
(iii)

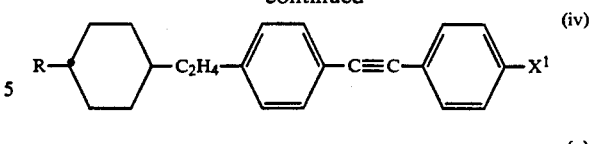
(iv)

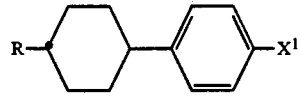
(v)

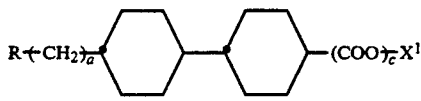
(vi)

(vii)

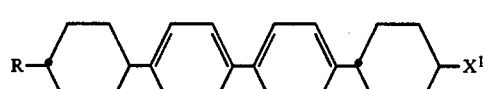
(viii)

(ix)

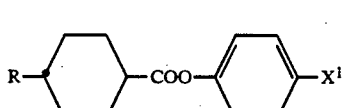
(x)

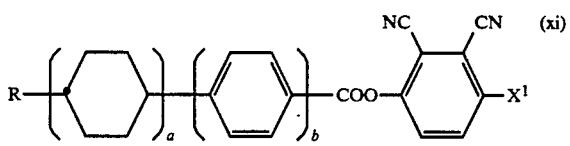
(xi)

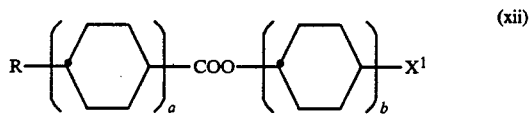
(xii)

In these formulas (i) to (xii), R and $X^1$ each independently represent an alkyl group, an alkoxy group, an alkenyl group or an alkenyloxy group each of 1 to 10 carbon atoms, a and b each represent 0, 1 and 2, c represents 0 or 1 and when $X^1$ represents an alkoxy group or an alkenyloxy group, c represents 0.

PREPARATION OF THE COMPOUND OF THE INVENTION

Preparation of the compound of the formula (I) of the present invention will be described below.

The compound of the formula (I) is divided into the following two groups according to its preparation:

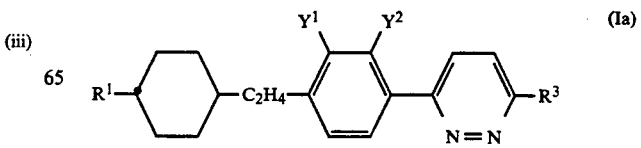
(Ia)

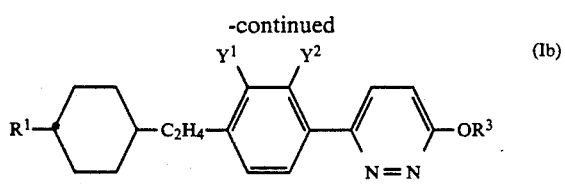

In the above formulas, $R^1$, $Y^1$ and $Y^2$ are as defined above, and $R^3$ represents an alkyl group of 1 to 15 carbon atoms.

Preparation methods of compounds (Ia) and (Ib) are exemplified as follows.

Preparation of the compound of the formula (Ia):

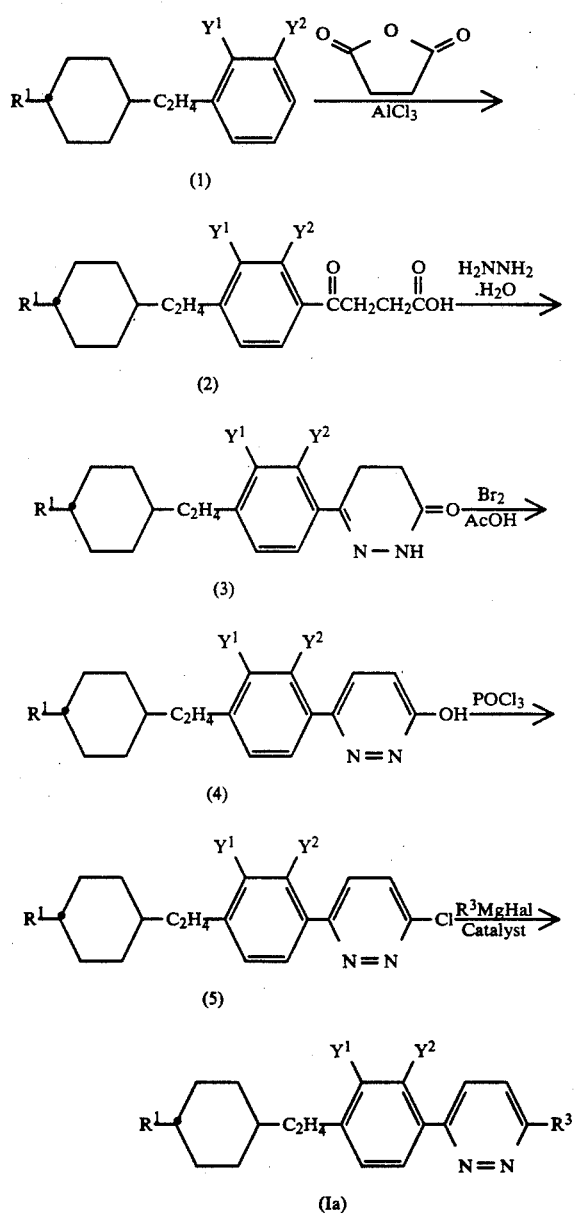

Preparation of the compound of the formula (Ib):

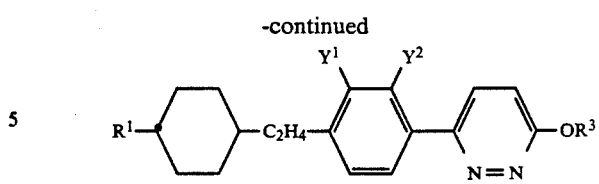

In the above equations, $R^1$, $R^2$, $R^3$, $Y^1$ and $Y^2$ are as defined above and Hal represents a halogen atom.

An ethane derivative (1) is reacted with succinic acid anhydride in the presence of aluminum chloride according to a method described in the literature (Z. Chem., 17 (9) 333 (1977)) to obtain a compound (2). The compound (2) is then reacted with hydrazine monohydrate to obtain a cyclized compound (3), subjecting this compound to dehydrogenation reaction with bromine in acetic acid solvent to obtain a compound (4), reacting this compound with phosphorus oxychloride to obtain a chlorinated compound (5), and further reacting this compound with a Grignard reagent prepared from an alkyl halide and magnesium in the presence of a catalyst of Ni(dppp)Cl$_2$, if desired, to obtain a compound (Ia) corresponding to the formula (I) wherein $R^2$ represents an alkyl group. Further, by reacting the above compound (5) with a sodium alkoxide, a compound (Ib) corresponding to the formula (I) wherein $R^2$ represents an alkoxy group can be obtained.

The present invention will be described in more detail by way of Examples, but it should not be construed to be limited thereto.

In these Examples, C-S$_A$ point represents crystals-mectic A phase transition point and S$_A$-I point represents smectic A phase-isotropic liquid phase transition point. The symbol ( ) indicates monotropic phase transition.

EXAMPLE 1

Preparation of 3-(4-(2-(trans-4-ethylcyclohexyl)ethyl)phenyl)-6-heptyloxypyridazine (a compound of the formula (I) wherein $R^1$=C$_2$H$_5$, $R^2$=OC$_7$H$_{15}$ and $Y^1$=Y$^2$=H) (Compound No. 5-14).

A mixture of 1-phenyl-2-(trans-4-ethylcyclohexyl)ethane (200.0 g, 0.93 mol), pulverized succinic acid anhydride (111.6 g, 1.11 mol) and CS$_2$ (500 ml) was cooled with ice down to 0° to 5° C. Pulverized anhydrous aluminum chloride (248.0 g, 1.86 mol) was gradually added to the mixture. After removing the ice bath, the mixture was agitated for one hour and successively agitated for 2 hours on a water bath at 60° C. The resulting material was allowed to stand overnight. The reaction material was poured into a mixture of ice (500 g) and 6N-HCl (300 ml). The mixture was agitated sufficiently and CS$_2$ and water were distilled off on a water bath, to obtain a residue. Toluene was added to the residue and then heated under reflux. After separating water by means of a DeanStoke type water separator, the resulting liquid was filtered off while hot and recrystallized to obtain the following 3-(4-(2-(trans-4-ethylcyclohexyl)ethyl)benzoyl)propanic acid (214 g, m.p.: 141.2°–142.6° C.).

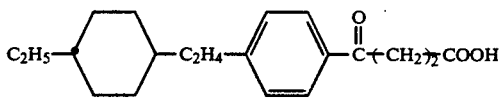

To this compound was added a mixture of 80% hydrazine hydrate (132.9 g) and water (600 ml). The mixture was agitated on a water bath at 60° C., to form crystals in the vessel after a while. After further agitating for about 2 hours, the resulting material was allowed to cool down to room temperature. The resulting crystals were filtered and recrystallized from a mixture of ethyl acetate (0.5 l) and ethanol (1.5 l) to obtain 3-(4-(2-(trans-4-ethylcyclohexyl)ethyl)phenyl)-4,5-dihydropyridazine-6-one (183 g) as follows:

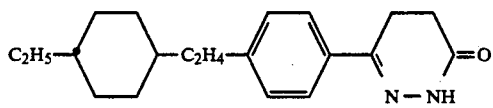

This compound exhibited monotropic liquid crystal phase and had a m.p. of 189.5° C. and a ($S_A$-I) point of 174.7° C.

This compound was dissolved in acetic acid (400 ml) with stirring on a water bath at 80° C. Bromine (129 g) dissolved in acetic acid (150 ml) was slowly dropwise added to the solution. After finishing the dropwise addition of bromine when the solution was colored by the red color of bromine midway during the dropwise addition, the solution was allowed to cool down to room temperature to form solids in the vessel. The solids were filtered and recrystallized from toluene to obtain 3-(4-(2-(trans-4-ethylcyclohexyl)ethyl)phenyl)pyridazine 6-one as follows.

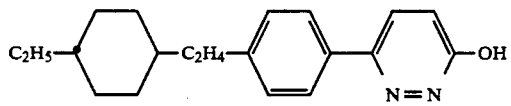

This compound exhibited monotropic liquid crystal phase and had a m.p. of 224.3° C. and a ($S_A$-I) point of 210° C.

A mixture obtained by adding phosphorus oxychloride (796.4 g) and N,N-diethylaniline (10 ml) to the above compound was heated under reflux for 3 hours. After distilling off excess phosphorus oxychloride under reduced pressure, the residue was poured in ice, and the resulting solids were filtered and recrystallized from toluene to obtain 3-(4-(2-(trans-4-ethylcyclohexyl)ethyl)phenyl)-6-chloropyridazine (130 g) as follows.

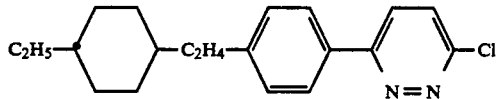

This compound exhibited monotropic liquid crystal phase and had a m.p. of 186.9° C. and a (N-I) point of 180.6° C.

A solution of n-heptanol (3.5 g) in toluene (50 ml) was dropwise added to a suspension of sodium hydride (about 55%) (1.5 g) in toluene (50 ml). The mixture was agitated for 30 minutes, dropwise adding a solution of 3-(4-(2-(trans-4-ethylcyclohexyl)ethyl)phenyl)-6-chloropyridazine (5 g) obtained above, in toluene (100 ml), heating the mixture under reflux for 3 hours. The reaction solution was poured in water. The resulting organic layer was washed with water until the organic layer became neutral. After drying it over anhydrous magnesium sulfate, distilling off the solvent under reduced pressure and recrystallizing the residue from ethanol, the captioned 3-(4-(2-(trans-4-ethylcyclohexyl)ethyl)phenyl)-6-heptyloxypyridazine (3.7 g) was obtained.

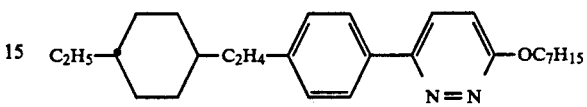

This compound had a C-$S_A$ point of 136.6° C. and a $S_A$-I point of 147.5° C.

The following compounds are prepared in the same manner as in Example 1:

| | |
|---|---|
| 3-(4-(2-(Trans-4-ethylcyclohexyl)ethyl)phenyl)-6-ethyloxypyridazine (m.p. 157.8° C.) | (5-9) |
| 3-(4-(2-(Trans-4-ethylcyclohexyl)ethyl)phenyl)-6-propyloxypyridazine (m.p. 162.7° C.) | (5-10) |
| 3-(4-(2-(Trans-4-ethylcyclohexyl)ethyl)phenyl)-6-butyloxypyridazine (m.p. 151.9° C., $S_A$-I point 148.5° C.) | (5-11) |
| 3-(4-(2-(Trans-4-ethylcyclohexyl)ethyl)phenyl)-6-pentyloxypyridazine (m.p. 148.1° C., $S_A$-I point 147.0° C.) | (5-12) |
| 3-(4-(2-(rrans-4-propylcyclohexyl)ethyl)phenyl)-6-ethyloxypyridazine | (5-16) |
| 3-(4-(2-(Trans-4-propylcyclohexyl)ethyl)phenyl)-6-propyloxypyridazine | (5-17) |
| 3-(4-(2-(Trans-4-propylcyclohexyl)ethyl)phenyl)-6-butyloxypyridazine | (5-18) |
| 3-(4-(2-(Trans-4-propylcyclohexyl)ethyl)phenyl)-6-pentyloxypyridazine (C-$S_A$ point 150.3° C., $S_A$-I point 165.4° C.) | (5-19) |
| 3-(4-(2-(Trans-4-butylcyclohexyl)ethyl)phenyl)-6-ethyloxypyridazine | (5-23) |
| 3-(4-(2-(Trans-4-butylcyclohexyl)ethyl)phenyl)-6-propyloxypyridazine | (5-24) |
| 3-(4-(2-(Trans-4-butylcyclohexyl)ethyl)phenyl)-6-butyloxypyridazine | (5-25) |
| 3-(4-(2-(Trans-4-butylcyclohexyl)ethyl)phenyl)-6-pentyloxypyridazine | (5-26) |
| 3-(4-(2-(Trans-4-pentylcyclohexyl)ethyl)phenyl)-6-ethyloxypyridazine | (5-30) |
| 3-(4-(2-(Trans-4-pentylcyclohexyl)ethyl)phenyl)-6-propyloxypyridazine | (5-31) |
| 3-(4-(2-(Trans-4-pentylcyclohexyl)ethyl)phenyl)-6-butyloxypyridazine | (5-32) |
| 3-(4-(2-(Trans-4-pentylcyclohexyl)ethyl)phenyl)-6-pentyloxypyridazine | (5-33) |
| 3-(2-Fluoro-4-(2-(trans-4-ethylcyclohexyl)ethyl)phenyl)-6-ethyloxypyridazine | (6-9) |
| 3-(2-Fluoro-4-(2-(trans-4-ethylcyclohexyl)ethyl)phenyl)-6-propyloxypyridazine | (6-10) |
| 3-(2-Fluoro-4-(2-(trans-4-ethylcyclohexyl)ethyl)phenyl)-6-butyloxypyridazine | (6-11) |
| 3-(2-Fluoro-4-(2-(trans-4-ethylcyclohexyl)ethyl)phenyl)-6-pentyloxypyridazine | (6-12) |
| 3-(2-Fluoro-4-(2-(trans-4-propylcyclohexyl)ethyl)phenyl)-6-ethyloxypyridazine | (6-16) |
| 3-(2-Fluoro-4-(2-(trans-4-propylcyclohexyl)ethyl)phenyl)-6-propyloxypyridazine | (6-17) |
| 3-(2-Fluoro-4-(2-(trans-4-propylcyclohexyl)ethyl)phenyl)-6-butyloxypyridazine | (6-18) |
| 3-(2-Fluoro-4-(2-(trans-4-propylcyclohexyl)ethyl)phenyl)-6-pentyloxypyridazine | (6-19) |
| 3-(2-Fluoro-4-(2-(trans-4-butylcyclohexyl)ethyl)phenyl)-6-ethyloxypyridazine | (6-23) |
| 3-(2-Fluoro-4-(2-(trans-4-butylcyclohexyl)ethyl)phenyl)-6-propyloxypyridazine | (6-24) |

| | |
|---|---|
| 3-(2-Fluoro-4-(2-(trans-4-butylcyclohexyl)ethyl)-phenyl)-6-butyloxypyridazine | (6-25) |
| 3-(2-Fluoro-4-(2-(trans-4-butylcyclohexyl)ethyl)-phenyl)-6-pentyloxypyridazine | (6-26) |
| 3-(2-Fluoro-4-(2-(trans-4-pentylcyclohexyl)ethyl)-phenyl)-6-ethyloxypyridazine | (6-30) |
| 3-(2-Fluoro-4-(2-(trans-4-pentylcyclohexyl)ethyl)-phenyl)-6-propyloxypyridazine | (6-31) |
| 3-(2-Fluoro-4-(2-(trans-4-pentylcyclohexyl)ethyl)-phenyl)-6-butyloxypyridazine | (6-32) |
| 3-(2-Fluoro-4-(2-(trans-4-pentylcyclohexyl)ethyl)-phenyl)-6-pentyloxypyridazine | (6-33) |
| 3-(3-Fluoro-4-(2-(trans-4-ethylcyclohexyl)ethyl)-phenyl)-6-ethyloxypyridazine | (7-9) |
| 3-(3-Fluoro-4-(2-(trans-4-ethylcyclohexyl)ethyl)-phenyl)-6-propyloxypyridazine | (7-10) |
| 3-(3-Fluoro-4-(2-(trans-4-ethylcyclohexyl)ethyl)-phenyl)-6-butyloxypyridazine | (7-11) |
| 3-(3-Fluoro-4-(2-(trans-4-ethylcyclohexyl)ethyl)-phenyl)-6-pentyloxypyridazine | (7-12) |
| 3-(3-Fluoro-4-(2-(trans-4-propylcyclohexyl)ethyl)-phenyl)-6-ethyloxypyridazine | (7-16) |
| 3-(3-Fluoro-4-(2-(trans-4-propylcyclohexyl)ethyl)-phenyl)-6-propyloxypyridazine | (7-17) |
| 3-(3-Fluoro-4-(2-(trans-4-propylcyclohexyl)ethyl)-phenyl)-6-butyoxypyridazine | (7-18) |
| 3-(3-Fluoro-4-(2-(trans-4-propylcyclohexyl)ethyl)-phenyl)-6-pentyloxypyridazine | (7-19) |
| 3-(3-Fluoro-4-(2-(trans-4-butylcyclohexyl)ethyl)-phenyl)-6-ethyloxypyridazine | (7-23) |
| 3-(3-Fluoro-4-(2-(trans-4-butylcyclohexyl)ethyl)-phenyl)-6-propyloxypyridazine | (7-24) |
| 3-(3-Fluoro-4-(2-(trans-4-butylcyclohexyl)ethyl)-phenyl)-6-butyloxypyridazine | (7-25) |
| 3-(3-Fluoro-4-(2-(trans-4-butylcyclohexyl)ethyl)-phenyl)-6-pentyloxypyridazine | (7-26) |
| 3-(3-Fluoro-4-(2-(trans-4-pentylcyclohexyl)ethyl)-phenyl)-6-ethyloxypyridazine | (7-30) |
| 3-(3-Fluoro-4-(2-(trans-4-pentylcyclohexyl)ethyl)-phenyl)-6-propyloxypyridazine | (7-31) |
| 3-(3-Fluoro-4-(2-(trans-4-pentylcyclohexyl)ethyl)-phenyl)-6-butyloxypyridazine | (7-32) |
| 3-(3-Fluoro-4-(2-(trans-4-pentylcyclohexyl)ethyl)-phenyl)-6-pentyloxypyridazine | (7-33) |
| 3-(2,3-Difluoro-4-(2-(trans-4-propylcyclohexyl)-ethyl)phenyl)-6-ethyloxypyridazine | (8-16) |
| 3-(2,3-Difluoro-4-(2-(trans-4-propylcyclohexyl)-ethyl)phenyl)-6-propyloxypyridazine | (8-17) |
| 3-(2,3-Difluoro-4-(2-(trans-4-propylcyclohexyl)-ethyl)phenyl)-6-butyloxypyridazine | (8-18) |
| 3-(2,3-Difluoro-4-(2-(trans-4-propylcyclohexyl)-ethyl)phenyl)-6-pentyloxypyridazine | (8-19) |
| 3-(2,3-Difluoro-4-(2-(trans-4-butylcyclohexyl)-ethyl)phenyl)-6-ethyloxypyridazine | (8-23) |
| 3-(2,3-Difluoro-4-(2-(trans-4-butylcyclohexyl)-ethyl)phenyl)-6-propyloxypyridazine | (8-24) |
| 3-(2,3-Difluoro-4-(2-(trans-4-butylcyclohexyl)ethyl)-phenyl)-6-butyloxypyridazine | (8-25) |
| 3-(2,3-Difluoro-4-(2-(trans-4-butylcyclohexyl)ethyl)-phenyl)-6-pentyloxypyridazine | (8-26) |
| 3-(2,3-Difluoro-4-(2-(trans-4-pentylcyclohexyl)ethyl)-phenyl)-6-ethyloxypyridazine | (8-30) |
| 3-(2,3-Difluoro-4-(2-(trans-4-pentylcyclohexyl)ethyl)-phenyl)-6-propyloxypyridazine | (8-31) |
| 3-(2,3-Difluoro-4-(2-(trans-4-pentylcyclohexyl)ethyl)-phenyl)-6-butyloxypyridazine | (8-32) |
| 3-(2,3-Difluoro-4-(2-(trans-4-pentylcyclohexyl)ethyl)-phenyl)-6-pentyloxypyridazine | (8-33) |

EXAMPLE 2

3-(4-(2-trans-4-ethylcyclohexyl)phenyl)-6-chloropyridazine which is an intermediate obtained in Example 1 (corresponding to Compound (5)) (20 g) was dissolved in tetrahydrofurane (100 ml) to obtain a solution. The solution was cooled in an ice bath, adding Ni(dppp)Cl$_2$(dichloro1,3-bis(diphenylphosphino)propane nickel)(0.2 g), and agitating for 15 minutes. To the resulting mixture was then dropwise added a Grignard reagent prepared from ethyl bromide (6.5 g) and magnesium, and the mixture was agitated in an ice bath for 2 hours, and successively agitated at room temperature for 2 hours. The resulting material was allowed to stand overnight. After adding toluene (200 ml) to the resulting material, 6N-hydrochloric acid was further added to obtain a separated organic phase. The organic phase was washed with water to make it neutral, dried over magnesium sulfate, and toluene was distilled off, to obtain a residue. The residue was purified according to column chromatography with activated alumina (30 g) using toluene as an eluent and twice recrystallizing from ethyl acetate (150 ml) to obtain 3-(4-(2-(trans-4-ethylcyclohexyl)ethyl)phenyl)-6-ethylpyridaxine (Compound No. 1-9)

The following compounds are prepared in the same manner as in Example 2:

| | |
|---|---|
| 3-(4-(2-(Trans-4-ethylcyclohexyl)ethyl)phenyl)-6-propylpyridazine | (1-10) |
| 3-(4-(2-(Trans-4-ethylcyclohexyl)ethyl)phenyl)-6-butylpyridazine | (1-11) |
| 3-(4-(2-(Trans-4-ethylcyclohexyl)ethyl)phenyl)-6-pentylpyridazine | (1-12) |
| 3-(4-(2-(Trans-4-propylcyclohexyl)ethyl)phenyl)-6-ethylpyridazine | (1-16) |
| 3-(4-(2-(Trans-4-propylcyclohexyl)ethyl)phenyl)-6-propylpyridazine | (1-17) |
| 3-(4-(2-(Trans-4-propylcyclohexyl)ethyl)phenyl)-6-butylpyridazine | (1-18) |
| 3-(4-(2-(Trans-4-propylcyclohexyl)ethyl)phenyl)-6-pentylpyridazine | (1-19) |
| 3-(4-(2-Trans-4-butylcyclohexyl)ethyl)phenyl-6-ethylpyridazine | (1-23) |
| 3-(4-(2-(Trans-4-butylcyclohexyl)ethyl)phenyl)-6-propylpyridazine | (1-24) |
| 3-(4-(2-(Trans-4-butylcyclohexyl)ethyl)phenyl)-6-butylpyridazine | (1-25) |
| 3-(4-(2-(Trans-4-butylcyclohexyl)ethyl)phenyl)-6-pentylpyridazine | (1-26) |
| 3-(4-(2-(Trans-4-pentylcyclohexyl)ethyl)phenyl)-6-ethylpyridazine | (1-30) |
| 3-(4-(2-(Trans-4-pentylcyclohexyl)ethyl)phenyl)-6-propylpyridazine | (1-31) |
| 3-(4-(2-(Trans-4-pentylcyclohexyl)ethyl)phenyl)-6-butylpyridazine | (1-32) |
| 3-(4-(2-(Trans-4-pentylcyclohexyl)ethyl)phenyl)-6-pentylpyridazine | (1-33) |
| 3-(2-Fluoro-4-(2-(trans-4-ethylcyclohexyl)ethyl)-phenyl)-6-ethylpyridazine | (2-9) |
| 3-(2-Fluoro-4-(2-(trans-4-ethylcyclohexyl)ethyl)-phenyl)-6-propylpyridazine | (2-10) |
| 3-(2-Fluoro-4-(2-(trans-4-ethylcyclohexyl)ethyl)-phenyl)-6-butylpyridazine | (2-11) |
| 3-(2-Fluoro-4-(2-(trans-4-ethylcyclohexyl)ethyl)-phenyl)-6-pentylpyridazine | (2-12) |
| 3-(2-Fluoro-4-(2-(trans-4-propylcyclohexyl)ethyl)-phenyl)-6-ethylpyridazine | (2-16) |
| 3-(2-Fluoro-4-(2-(trans-4-propylcyclohexyl)ethyl)-phenyl)-6-propylpyridaine | (2-17) |
| 3-(2-Fluoro-4-(2-(trans-4-propylcyclohexyl)ethyl)-phenyl)-6-butylpyridazine | (2-18) |
| 3-(2-Fluoro-4-(2-(trans-4-propylcyclohexyl)ethyl)-phenyl)-6-pentylpyridazine | (2-19) |
| 3-(2-Fluoro-4-(2-(trans-4-butylcyclohexyl)ethyl)-phenyl)-6-ethylpyridazine | (2-30) |
| 3-(2-Fluoro-4-(2-(trans-4-butylcyclohexyl)ethyl)-phenyl)-6-propylpyridazine | (2-31) |
| 3-(2-Fluoro-4-(2-(trans-4-butylcyclohexyl)ethyl)-phenyl)-6-butylpyridazine | (2-32) |
| 3-(2-Fluoro-4-(2-(trans-4-butylcyclohexyl)ethyl)-phenyl)-6-butylpyridazine | (2-33) |
| 3-(2-Fluoro-4-(2-(trans-4-butylcyclohexyl)ethyl)-phenyl)-6-pentylpyridazine | (2-37) |
| 3-(2-Fluoro-4-(2-(trans-4-pentylcyclohexyl)ethyl)-phenyl)-6-ethylpyridazine | (2-38) |
| 3-(2-Fluoro-4-(2-(trans-4-pentylcyclohexyl)ethyl)-phenyl)-6-propylpyridazine | (2-39) |
| 3-(2-Fluoro-4-(2-(trans-4-pentylcyclohexyl)ethyl)-phenyl)-6-butylpyridazine | (2-40) |
| 3-(2-Fluoro-4-(2-(trans-4-pentylcyclohexyl)ethyl)- | |

| | |
|---|---|
| phenyl)-6-pentylpyridazine | |
| 3-(3-Fluoro-4-(2-(trans-4-ethylcyclohexyl)ethyl)-phenyl)-6-ethylpyridazine | (3-9) |
| 3-(3-Fluoro-4-(2-(trans-4-ethylcyclohexyl)ethyl)-phenyl)-6-propylpyridazine | (3-10) |
| 3-(3-Fluoro-4-(2-(trans-4-ethylcyclohexyl)ethyl)-phenyl)-6-butylpyridazine | (3-11) |
| 3-(3-Fluoro-4-(2-(trans-4-ethylcyclohexyl)ethyl)-phenyl)-6-pentylpyridazine | (3-12) |
| 3-(3-Fluoro-4-(2-(trans-4-propylcyclohexyl)ethyl)-phenyl)-6-ethylpyridazine | (3-16) |
| 3-(3-Fluoro-4-(2-(trans-4-propylcyclohexyl)ethyl)-phenyl)-6-propylpyridazine | (3-17) |
| 3-(3-Fluoro-4-(2-(trans-4-propylcyclohexyl)ethyl)-phenyl)-6-butylpyridazine | (3-18) |
| 3-(3-Fluoro-4-(2-(trans-4-propylcyclohexyl)ethyl)-phenyl)-6-pentylpyridazine | (3-19) |
| 3-(3-Fluoro-4-(2 (trans-4-butylcyclohexyl)ethyl)-phenyl)-6-ethylpyridazine | (3-23) |
| 3-(3-Fluoro-4-(2-(trans-4-butylcyclohexyl)ethyl)-phenyl)-6-propylpyridazine | (3-24) |
| 3-(3-Fluoro-4-(2-(trans-4-butylcyclohexyl)ethyl)-phenyl)-6-butylpyridazine | (3-25) |
| 3-(3-Fluoro-4-(2-(trans-4-butylcyclohexyl)ethyl)-phenyl)-6-pentylpyridazine | (3-26) |
| 3-(3-Fluoro-4-(2-(trans-4-pentylcyclohexyl)ethyl)-phenyl)-6-ethylpyridazine | (3-30) |
| 3-(3-Fluoro-4-(2-(trans-4-pentylcyclohexyl)ethyl)-phenyl)-6-proplpyridazine | (3-31) |
| 3-(3-Fluoro-4-(2-(trans-4-pentylcyclohexyl)ethyl)-phenyl)-6-butylpyridazine | (3-32) |
| 3-(3-Fluoro-4-(2-(trans-4-pentylcyclohexyl)ethyl)-phenyl)-6-pentylpyridazine | (3-33) |
| 3-(2,3-Difluoro-4-(2-(trans-4-ethylcyclohexyl)-ethyl)phenyl)-6-ethylpyridazine | (4-9) |
| 3-(2,3-Difluoro-4-(2-(trans-4-ethylcyclohexyl)-ethyl)phenyl)-6-propylpyridazine | (4-10) |
| 3-(2,3-Difluoro-4-(2-(trans-4-ethylcyclohexyl)-ethyl)phenyl)-6-butylpyridazine | (4-11) |
| 3-(2,3-Difluoro-4-(2-(trans-4-ethylcyclohexyl)-ethyl)phenyl)-6-pentylpyridazine | (4-12) |
| 3-(2,3-Difluoro-4-(2-(trans-4-propylcyclohexyl)-ethyl)phenyl)-6-ethylpyridazine | (4-16) |
| 3-(2,3-Difluoro-4-(2-(trans-4-propylcyclohexyl)-ethyl)phenyl)-6-propylpyridazine | (4-17) |
| 3-(2,3-Difluoro-4-(2-(trans-4-propylcyclohexyl)-ethyl)phenyl)-6-butylpyridazine | (4-18) |
| 3-(2,3-Difluoro-4-(2-(trans-4-propylcyclohexyl)-ethyl)phenyl)-6-pentylpyridazine | (4-19) |
| 3-(2,3-Difluoro-4-(2-(trans-4-butylcyclohexyl)-ethyl)phenyl)-6-ethylpyridazine | (4-23) |
| 3-(2,3-Difluoro-4-(2-(trans-4-butylcyclohexyl)-ethyl)phenyl)-6-propylpyridazine | (4-24) |
| 3-(2,3-Difluoro-4-(2-(trans-4-butylcyclohexyl)-ethyl)phenyl)-6-butylpyridazine | (4-25) |
| 3-(2,3-Difluoro-4-(2-(trans-4-butylcyclohexyl)-ethyl)phenyl)-6-pentylpyridazine | (4-26) |
| 3-(2,3-Difluoro-4-(2-(trans-4-pentylcyclohexyl)-ethyl)phenyl)-6-ethylpyridazine | (4-30) |
| 3-(2,3-Difluoro-4-(2-(trans-4-pentylcyclohexyl)-ethyl)phenyl)-6-propylpyridazine | (4-31) |
| 3-(2,3-Difluoro-4-(2-(trans-4-pentylcyclohexyl)-ethyl)phenyl)-6-butylpyridazine | (4-32) |
| 3-(2,3-Difluoro-4-(2-(trans-4-pentylcyclohexyl)-ethyl)phenyl)-6-pentylpyridazine | (4-33) |

EXAMPLE 3 (USE EXAMPLE 1)

A liquid crystal composition (A) consisting of

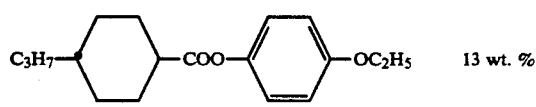

13 wt. %

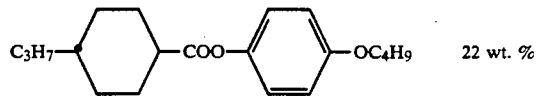

22 wt. %

$C_4H_9$—⬡—COO—⌬—$OC_2H_5$  16 wt. %

$C_5H_{11}$—⬡—COO—⌬—$OCH_3$  16 wt. %

$C_5H_{11}$—⬡—COO—⌬—$OC_2H_5$  11 wt. %

$C_3H_7$—⬡—⌬—$OC_2H_5$  14 wt. %

$C_3H_7$—⬡—⌬—$OC_4H_9$  8 wt. % exhibited a N-I point of 64.0° C., a viscosity at 25° C. of 13.3 cP, a Δn of 0.085 and a Δε of −1.07.

To this liquid crystal composition (A) (90% by weight) was added 3-(4-(2-(trans-4-ethylcyclohexyl)e-thyl)phenyl)6-butyloxypyridaxine as one of the compounds of the present invention (Compound No. 5-11) (10% by weight). The resulting composition exhibited a N-I point raised to 70.0° C., a viscosity at 25° C. slightly raised to 7.3 cP, a Δn raised to 0.093 and a Δε raised to −1.29.

As seen from this Example, the compound of the present invention has an effectiveness of raising the N-I point of the parent liquid crystal composition up to a practically sufficient value while suppressing the viscosity rise to the minimum and raising the absolute values of the Δn and Δε.

According to the present invention, there are provided a liquid crystalline compound having a large negative dielectric anisotropy value, a low viscosity and a large birefringence anisotropy value, and a liquid crystal composition suitable as an element constituting light switching elements.

What we claim is:

1. A liquid crystalline compound having a negative dielectric anisotropy value, expressed by the formula $$R^1-⬡-C_2H_4-\underset{}{⌬}^{Y^1\ Y^2}-R^2 \quad (I)$$
$$N-N$$

wherein $R^1$ and $R^2$ each independently represent a linear alkyl group or a linear alkoxy group each of 1 to 158 carbon atoms and $Y^1$ and $Y^2$ each independently represent H or F.

2. A liquid crystalline compound according to claim 1, wherein at least one of said $Y^1$ and $Y^2$ is F.

3. A liquid crystalline compound according to claim 1, wherein said $R^1$ represents a linear alkyl group of 2 to 5 carbon atoms.

4. A liquid crystal composition comprising at least two components at least one of which is a liquid crystalline compound as set forth in claim 1.

* * * * *